United States Patent [19]

Miller et al.

[11] Patent Number: 4,983,109

[45] Date of Patent: Jan. 8, 1991

[54] SPRAY HEAD ATTACHMENT FOR METERING GEAR HEAD

[75] Inventors: Scott R. Miller, Roswell; John M. Raterman; Roger A. Ziecker, both of Lawrenceville, all of Ga.

[73] Assignee: Nordson Corporation, Westlake, Ohio

[21] Appl. No.: 143,829

[22] Filed: Jan. 14, 1988

[51] Int. Cl.⁵ .......................... B05B 1/16; B05B 1/34
[52] U.S. Cl. .......................................... 425/7; 118/62; 118/63; 118/325; 222/263; 222/318; 239/125; 239/298; 239/553.5; 239/558; 239/562; 239/600; 264/12; 264/518; 264/DIG. 28; 425/72.1; 425/192; 425/326.1; 425/387.1
[58] Field of Search .................. 425/7, 10, 72.1, 72.2, 425/97, 130, 131.1, 131.5, 461, 462, 464, 217, 185, 192 R, 192 S, 376.1, 378.2, 379.6, 382.4, 166, 326.1, 387.1, 375; 188/685, 316, 385, 62, 63, 325; 264/171, 50 DIG. 75, 5, 11, 12, DIG. 28, 518; 222/146, 144.5, 255, 265, 330, 146.5, 318, 39, 263; 239/422–424, 426, 433, 76, 8, 124, 553.5–568, 405, 406, 296, 298; 65/5, 16

[56] References Cited

U.S. PATENT DOCUMENTS

| 721,900 | 3/1903 | Lassoe et al. ........................ 239/406 |
|---|---|---|
| 2,626,424 | 1/1953 | Hawthorne, Jr. ...................... 65/5 |
| 3,053,461 | 9/1962 | Inglis .................................... 239/411 |
| 3,152,923 | 10/1964 | Marshall et al. ..................... 118/685 |
| 3,502,763 | 3/1970 | Hartman .............................. 425/72.2 |
| 3,561,053 | 2/1971 | Pearson ............................... 425/192 |
| 3,690,518 | 9/1972 | Baker et al. .......................... 222/504 |
| 3,764,069 | 10/1973 | Runstadler, Jr. et al. ............. 239/8 |
| 3,825,379 | 7/1974 | Lohkamp et al. ................... 425/72.2 |
| 3,841,567 | 10/1974 | Drozek et al. ....................... 239/570 |
| 3,942,723 | 3/1976 | Langdon .............................. 425/72.2 |
| 4,144,011 | 3/1979 | Sponaugle ........................... 425/461 |
| 4,159,199 | 6/1979 | Levecque et al. .................... 65/5 |
| 4,185,981 | 1/1980 | Ohsato et al. ....................... 65/5 |
| 4,225,299 | 9/1980 | Roberts ............................... 425/72.2 |
| 4,291,157 | 8/1980 | Binoche ............................... 536/6.4 |
| 4,411,389 | 10/1983 | Harrison ............................. 239/427.5 |
| 4,416,600 | 11/1983 | Lecznar ............................... 425/7 |
| 4,445,833 | 5/1984 | Moriki et al. ........................ 425/131.5 |
| 4,470,789 | 9/1984 | Whittington et al. ............... 425/192 R |
| 4,483,812 | 11/1984 | Hahn et al. .......................... 425/131.1 |
| 4,526,733 | 7/1985 | Lau ..................................... 264/DIG. 75 |
| 4,545,507 | 10/1985 | Barall ................................. 222/255 |
| 4,687,137 | 8/1987 | Boger et al. ......................... 239/556 |
| 4,778,642 | 10/1988 | Lee et al. ............................. 425/72.1 |
| 4,785,996 | 11/1988 | Ziecker et al. ...................... 425/7 |

FOREIGN PATENT DOCUMENTS

| 1109198 | 8/1984 | U.S.S.R. ............................... 239/290 |
|---|---|---|
| 1240465 | 6/1986 | U.S.S.R. ............................... 239/290 |

OTHER PUBLICATIONS

"Spinning Pumps For the Production of Synthetic Fibres", Feinpruef GmbH, West Germany.
"Zenith Planetary Pumps", Zenith Nichols, Bulletin P-02.

Primary Examiner—Jeffery Thurlow
Assistant Examiner—Mathiea Vargot
Attorney, Agent, or Firm—Wood, Herron & Evans

[57] ABSTRACT

A spray head attachment adapted for use with a flow metering device such as a metering gear head is effective to discharge a plurality of spiral spray patterns of hot melt adhesive, in elongated strands or fibers, onto the backing sheet of a hygienic article. The spray head attachment includes a manifold having adhesive passageways connected to outlets of the metering gear head, air passageways connected to a source of pressurized air and recirculation passageways connected to a source of hot melt adhesive. Outlets of the adhesive and air passageways, and inlets of the recirculation passageways, are formed on a discharge surface of the manifold in groups or arrays, so that nozzles mounted to the manifold are each connected to one array of adhesive, air and recirculation passageways. Each nozzle is effective to discharge an adhesive bead and then impact the bead with jets of air directed tangentially relative to its periphery to form elongated adhesive strands or fibers and to impart a twisting motion to the fibers for deposition in a compact, spiral spray pattern onto the backing sheet of the hygienic article.

11 Claims, 3 Drawing Sheets

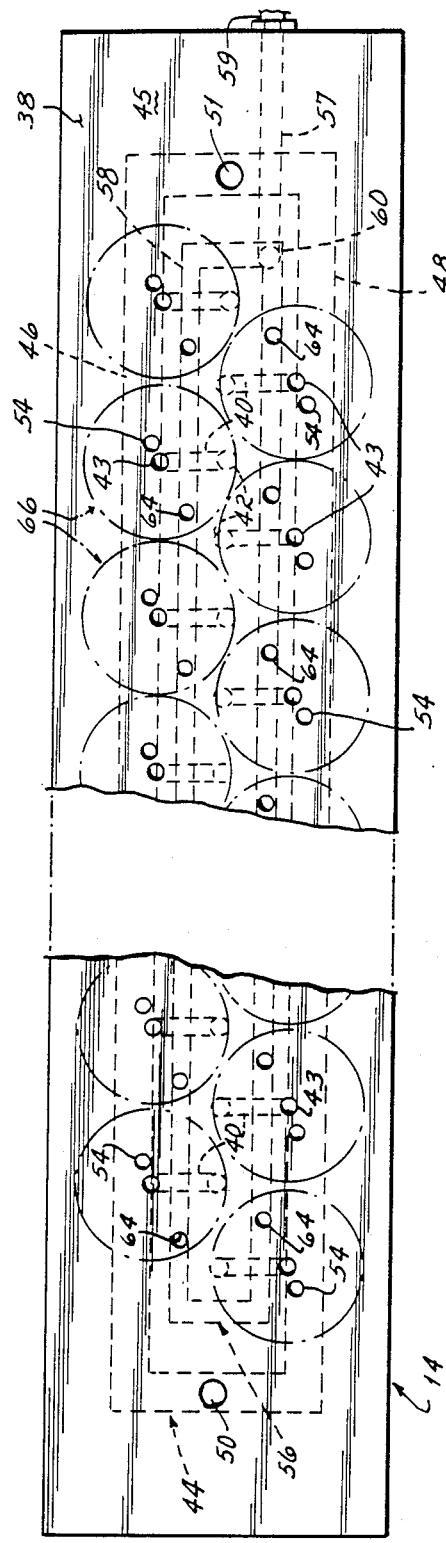
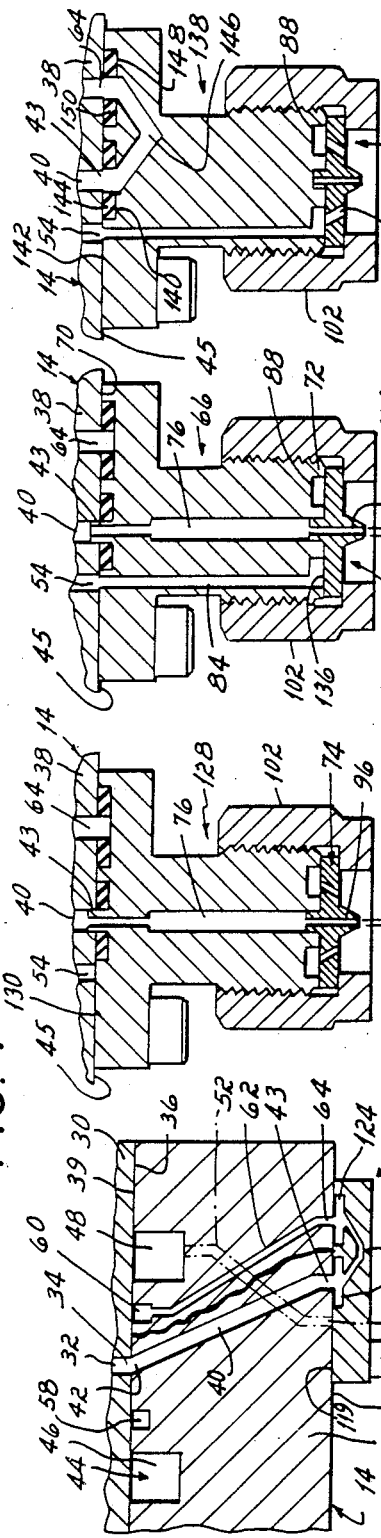

SPRAY HEAD ATTACHMENT FOR METERING GEAR HEAD

FIELD OF THE INVENTION

This invention relates to adhesive dispensing systems, and, more particularly, to a flow metering device such as a metering gear head having a spray head attachment for spraying a plurality of separate patterns of hot melt adhesive in the form of elongated, thin strands or fibers onto a substrate such as the backing sheet of hygienic articles.

BACKGROUND OF THE INVENTION

Hot melt thermoplastic adhesives have been widely used in industry for adhering many types of products, and are particularly useful in applications where quick setting time is advantageous. One application for hot melt adhesives which has been of considerable interest in recent years is the bonding of non-woven fibrous material to the backing sheet of hygienic articles such as disposable diapers, incontinence pads and similar articles.

In the prior art, the manufacture of disposable diapers, for example, has involved the application of multiple, parallel beads of pressure sensitive hot melt adhesive onto the backing sheet of the diaper so as to adhere the backing sheet to the non-woven, absorbent pad of the diaper. To ensure a good bond is obtained between the non-woven pad and backing sheet, and an acceptable visual appearance of the resulting product, the adhesive beads must be accurately positioned along the backing sheet and formed in a uniform width.

One apparatus commonly employed in the manufacture of disposable diapers and other hygienic articles is a metering gear head having a plurality of spaced discharge orifices, each supplied with adhesive from a gear pump, which are positioned relative to the backing sheet to apply parallel beads of adhesive thereto for subsequent attachment to a non-woven absorbent pad. The primary advantages of metering gear heads are that they provide for precise control of the quantity of adhesive dispensed, and accurately locate the adhesive beads on the backing sheet of the diaper, so that the resulting product has multiple adhesive beads of uniform size, width and spacing.

Despite these advantages, metering gear heads also present problems in the manufacture of disposable diapers and other hygienic articles which employ a backing sheet formed of polyethylene, polypropylene, polyurethane or similar materials. The specific heat of the hot melt adhesive discharged in the form of beads from metering gear heads onto the backing sheet has the potential to burn through the backing sheet or at least distort the material and produce an unacceptable product. While this problem can be reduced or overcome by increasing the thickness of the backing sheet, the added thickness increases the cost of the backing sheet. In addition, the adhesive beads discharged onto one side of the backing sheet are readily visible from its outer side which detracts from the appearance of the finished product.

Attempts have been made in the prior art to avoid the problem of burn through or distortion of the backing sheet of hygienic articles, caused by the heat of the hot melt adhesive beads applied thereto, without increasing the thickness of the material forming the backing sheet. In one prior art method, the hot melt thermoplastic adhesive is formed in elongated, thin strands or fibers which are deposited atop the non-woven layer of the article and then the non-woven layer is bonded to the backing sheet. The specific heat of the thin, elongated strands or fibers of adhesive is less than that of the relatively thicker and wider adhesive beads discharged from metering gear heads, and thus the problem of burn through or distortion of the backing sheets of hygienic articles is reduced so that thinner materials can be employed in the manufacture of the backing sheets. In addition, the thin fibers or strands of adhesive are essentially invisible through the backing sheet which produces a more aesthetically acceptable finished product.

Prior art spray devices capable of producing such elongated adhesive strands or fibers include a nozzle formed with an adhesive discharge opening and one or more air jet orifices through which a jet of air is ejected. A bead of adhesive is discharged from the adhesive discharge opening in the nozzle which is then impinged by the air jets to attenuate or stretch the adhesive bead forming thin fibers for deposition onto the substrate. Examples of spray devices of this general type are disclosed in U.S. Pat. Nos. 2,626,424 to Hawthorne, Jr.; 3,152,923 to Marshall et al; and, 4,185,981 to Ohsato et al.

Prior art spray devices of the type described above are also capable of accurately controlling the location of the spray patterns of elongated adhesive strands or fibers discharged onto the substrate, and these spray patterns are nearly invisible on the finished product. In the devices such as disclosed, for example, in the U.S. Pat. No. 2,626,424 patent to Hawthorne, Jr. and the U.S. Pat. No. 4,185,981 to Ohsato et al, the air jets are directed substantially tangent to the adhesive bead ejected from the discharge opening in the nozzle which rotates or twists the elongated adhesive fibers in a relatively tight, compact spiral spray pattern for application onto the substrate.

In a commercial disposable diaper production line, for example, conventional metering gear heads apply 32 or more individual, parallel beads of adhesive onto a moving backing sheet which is subsequently cut along both its width and length to form individual diapers. In applications of this type, prior art spray systems for spraying spiral patterns of adhesive fibers or strands, such as described above, are not entirely suitable. A separate nozzle is required in such systems to produce a spiral spray pattern adhesive fibers at each of the 32 locations where an adhesive bead had been applied by prior art metering gear heads. Whereas each discharge outlet which produces an adhesive bead in a metering gear head is directly supplied with adhesive from a separate supply line connected to a gear pump, the nozzles of prior art spiral spray systems are not directly connected to a pump. Instead, a number of nozzles are supplied with adhesive from a common supply line connected to a pump. Depending upon the pressure drop in such common supply lines from nozzle to nozzle, the quantity of adhesive discharged from each nozzle can vary. That is, the quantity of adhesive discharged from a given nozzle decreases as the pressure in the supply line at such nozzle decreases.

In order to produce an acceptable bond between the backing sheet and non-woven layer of a hygienic article, a predetermined minimum quantity of adhesive must be applied to the backing sheet by each nozzle of such prior art spiral spray systems. Although the problem of pressure drop within the adhesive supply lines of such spiral spray systems can be overcome by increasing the pump pressure so that the pressure in the supply lines at each nozzle location results in the discharge of at least the minimum required quantity of adhesive from each nozzle, this increase in pump pressure results in an overall increase of the total amount of adhesive discharged onto the backing sheet. This is because the pressure in the supply lines at some of the nozzles will be greater than that required to discharge the minimum amount of adhesive from such nozzles, and thus too much adhesive is applied to the backing sheet from these nozzles. This wastes adhesive and adds to the cost of the finished product.

SUMMARY OF THE INVENTION

It is therefore among the objectives of this invention to provide a system for applying adhesive to the backing sheet of a hygienic article such as a disposable diaper which provides for precise control of the quantity of adhesive dispensed, which avoids damage to the backing sheet of the article, which produces a hygienic article having an improved appearance and which is relatively economical and easy to retrofit on commercial production lines for hygienic articles such as disposable diapers.

These objectives are accomplished in a spray head attachment adapted to mount to a conventional flow metering device such as a metering gear head. The metering gear head includes a series of gear pumps which pump heated hot melt adhesive to a plurality of outlets formed on an outer surface of a manifold associated with the metering gear head. The spray head attachment comprises a second, distribution manifold which mounts onto the outer surface of the metering gear head manifold. This second, distribution manifold has a group of adhesive connector passageways each connected to an outlet of the metering gear head manifold, a group of air passageways connected to a source of pressurized air and a group of recirculation passageways which communicate with the source of hot melt adhesive, or, alternatively, the metering gear head manifold. All of these passageways terminate at a discharge surface of the distribution manifold and have orifices thereat arranged in arrays of three, i.e., an outlet of one adhesive passageway, an outlet of one air passageway and an inlet of one recirculation passageway are all located proximate one another on the discharge surface of the distribution manifold.

A plurality of nozzles are mounted to this discharge surface of the distribution manifold so that one array of adhesive, air and recirculation passageway orifices are connected to each nozzle. Adhesive discharged from the distribution manifold flows into each nozzle and is ejected as an adhesive bead from the discharge orifice of a nozzle attachment carried by the nozzle. Each nozzle attachment is formed with air jet bores connected via an air passageway in the nozzle to the air passageways in the distribution manifold, and these air jet bores are effective to direct air jets at the periphery of the adhesive bead ejected from the nozzle attachment to both stretch the bead to form elongated adhesive strands or fibers, and to impart a twisting motion to such fibers so that they are deposited in a controlled, spiral spray pattern upon the backing sheet of a hygienic article such as a disposable diaper.

The spray head attachment of this invention can be relatively easily retrofitted to standard metering gear heads which are now commonly used in the application of hot melt adhesive to the backing sheet of hygienic articles. This construction is advantageous in that it combines the accuracy of metering gear heads in dispensing precise quantities of hot melt adhesive, with spray nozzles capable of discharging spiral patterns of adhesive fibers onto the backing sheet which do not have sufficient specific heat to create problems of burn through or distortion of even relatively thin backing sheets. Moreover, the spiral patterns of adhesive fibers produced by the instant invention are not readily visible through the backing sheet, as are parallel adhesive beads produced by conventional metering gear heads, and this produces a more aesthetically acceptable finished product.

In the presently preferred embodiment, the spray head attachment herein is adapted for use with a metering gear head having four gear pumps each supplying hot melt adhesive to a group of eight adhesive supply passageways formed in a manifold associated with the metering gear head. A total of 32 outlets are formed on an outer surface of the manifold, one for each of the adhesive supply passageways.

The second, distribution manifold of the spray head attachment is mounted to the outer surface of the metering gear head manifold and has 32 adhesive connector passageways each formed with an inlet connected to an outlet of the metering gear head manifold, and a separate outlet formed on a discharge surface of the distribution manifold. An air channel is formed in the distribution manifold which is connected to a source of pressurized air. This air channel supplies pressurized air to a group of 32 air connector passageways formed in the distribution manifold each having an inlet at the air channel and an outlet on the discharge face of the distribution manifold. In addition, the distribution manifold is formed with a recirculation channel connected to the inlet of 32 recirculation passageways, each having an inlet on the discharge face of the distribution manifold.

A nozzle is mounted to the outer surface of the distribution manifold at each of the 32 locations where the orifices of an array of air, adhesive and recirculation passageways, respectively, terminate. In the preferred embodiment, the nozzles are each formed with an adhesive discharge passageway connected to the outlet of an adhesive connector passageway in the distribution manifold, an air discharge passageway connected to the outlet of an air connector passageway in the distribution manifold and a seal for sealing the inlet of a recirculation passageway. Hot melt adhesive from the metering gear head is therefore transmitted through the metering gear head manifold, into the adhesive passageways of the second, distribution manifold and through the adhesive discharge passageway in the nozzles for discharge onto the backing sheet of the hygienic article. Pressurized air flowing through the air supply channel in the distribution manifold is transmitted through the air passageways therein and into the air discharge passageways of each nozzle.

The nozzles each mount a nozzle attachment of the type disclosed in co-pending U.S. patent application Ser. No. 07/041,712, filed Apr. 23, 1987, now U.S. Pat. No. 4,785,996, and entitled "Adhesive Spray Gun and Nozzle Attachment" to Ziecker et al. The nozzle attachment is a one-piece annular plate which is mounted by a cap to one end of each of the nozzles carried by the distribution manifold. The nozzle attachment is formed with a throughbore adapted to connect to the adhesive discharge passageway in the nozzle, and a plurality of spaced air jet bores which communicate with the air discharge passageway in the nozzle. Adhesive transmitted through the nozzle is ejected as a bead from the throughbore in the nozzle attachment and this bead is impacted by air jets discharged from the spaced air jet bores therein. The air jets are directed tangentially relative to the adhesive bead to both stretch the bead forming elongated hot melt adhesive fibers, and to impart a twisting, rotating motion to the adhesive fibers so that they are deposited in a controlled, spiral spray pattern upon the backing sheet.

Thirty-two overlapping patterns of hot melt adhesive fibers, one from each of the nozzles carried by the distribution manifold, can thus be applied to the backing sheet of a hygienic article such as a disposable diaper by the adhesive spraying system herein. It is contemplated, however, that in some applications less than 32 spiral patterns of adhesive fibers would be required thus making it necessary to block the flow of adhesive from some of the nozzles carried on the distribution manifold. Alternatively, it may be desirable to discharge a thin bead of adhesive onto the backing sheet from some of the nozzles, and a spiral pattern of adhesive in fiber form from other nozzles. In a further alternative embodiment of the method of operating the spraying system herein, it is contemplated that one or more of the outermost nozzles on the distribution manifold would be modified to spray only air toward the backing sheet. This would ensure that the adhesive spray patterns on the outer edges of the distribution manifold are uneffected by conditions exterior to the production line.

Each of the alternative methods of operating the adhesive spray system of this invention is accomplished by modifying either the nozzle carried by the distribution manifold of the spray head attachment or the nozzle attachment for the nozzles. For example, in order to block the flow of adhesive and air from one or more locations on the distribution manifold, a blocking plate is mounted thereat which seals the air passageway. The blocking plate is formed with an internal passageway which interconnects the adhesive connector passageway in the distribution manifold with the inlet of the recirculation passageway therein to return the hot melt adhesive to the source.

In those applications wherein it is desired to discharge a thin bead of adhesive onto at least some locations along the backing sheet, one or more of the nozzles carried by the distribution manifold is modified to eliminate the air passageway therein so that only an adhesive bead is ejected from the nozzle attachment of the nozzle. In an alternative embodiment, nozzles having both adhesive and air discharge passageways are fitted with modified nozzle attachments formed without air jet bores. These nozzle attachments block the flow of air from the air discharge passageway in the nozzle, but permit the discharge of an adhesive bead through the adhesive discharge opening formed in the nozzle attachments.

If a given application requires an air flow from one or more of the nozzle locations but no adhesive flow, one or more of the nozzles is formed without an adhesive discharge passageway. In this embodiment, air is permitted to flow through the air discharge passageway in the nozzle to the air jet bores of the nozzle attachment, but a recirculation passageway is formed in the nozzle to receive adhesive from the adhesive connector passageway in the distribution manifold and recirculate such adhesive into the inlet of the recirculation passageways thereof for return to the adhesive source.

DESCRIPTION OF THE DRAWINGS

The structure, operation and advantages of the presently preferred embodiment of this invention will become further apparent upon consideration of the following description, taken in conjunction with the accompanying drawings, wherein:

FIG. 4 is a partial bottom view of the distribution manifold taken generally along line 4—4 of FIG. 3;

FIG. 5 is a cross sectional view similar to FIG. 3 of a blocking plate mounted to the distribution manifold;

FIG. 6 is an alternative embodiment of the nozzle shown in FIG. 3 for dispensing adhesive only;

FIG. 7 is a still further alternative embodiment of the nozzles shown in FIGS. 3 and 5 for dispensing adhesive only; and FIG. 8 is a view similar to FIG. 3 showing an alternative embodiment of the nozzle herein for spraying air only.

DETAILED DESCRIPTION OF THE INVENTION

Figure 1:
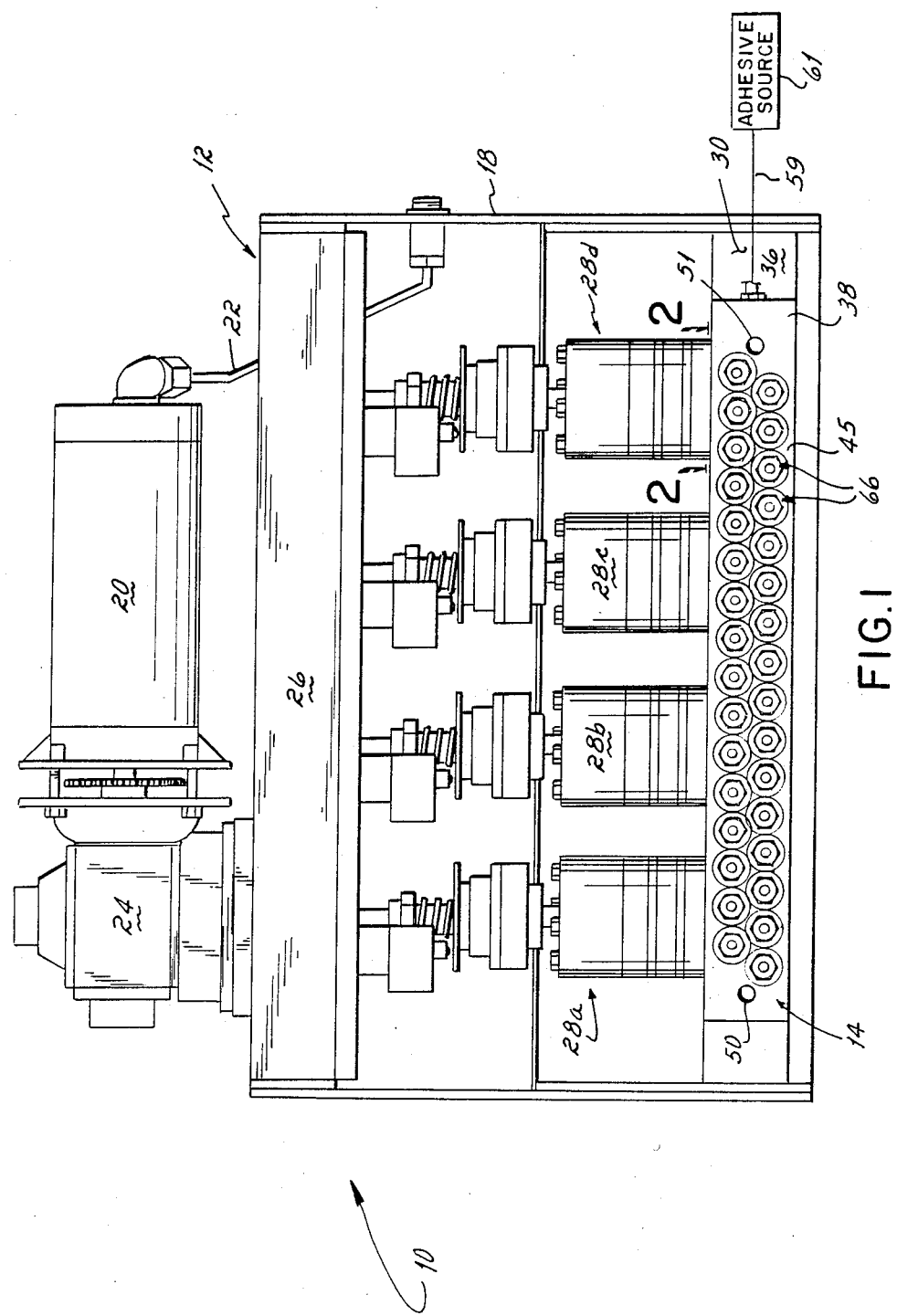
FIG. 1 is a bottom view of the metering gear head and spray head attachment of this invention.

Referring now to FIG. 1, a hot melt adhesive dispensing system 10 is illustrated which comprises a flow metering device such as a metering gear head 12 and a spray head attachment 14 mounted to the metering gear head 12. The dispensing system 10 is operable to discharge a plurality of patterns of hot melt adhesive, preferably in the form of elongated strands or fibers, onto the surface of a substrate such as the backing sheet 16 used in the formation of hygienic articles including disposable diapers. See FIG. 3. The backing sheet 16 of such articles is typically formed of a moisture impervious, heat sensitive material such as polypropylene, polyethylene or polyurethane.

The metering gear head 12 is commercially available and is of the general type used on production lines for hygienic articles such as disposable diapers. The structural details of the metering gear head 12 form no part of this invention per se and thus only the general construction of the metering gear 12 is illustrated and discussed herein. The metering gear head 12 comprises a housing 18 having a top surface which mounts an electric motor 20 connected to an electric cable 22, and a gear reducer 24 which is drivingly connected to the output of motor 20. The output of the gear reducer 24 is connected to a transmission 26 which extends across the top of the housing 18 between its opposed sides. The transmission 26 is drivingly connected to four gear pumps 28a–d which are located in the interior of the housing 18.

Figure 2:
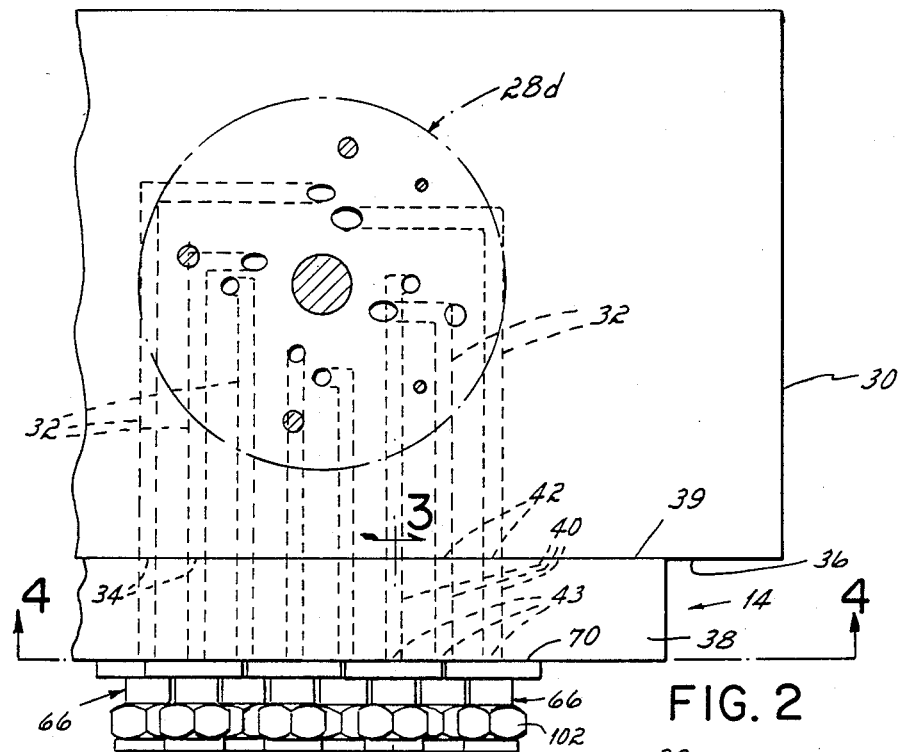
FIG. 2 is a cross sectional view of the connection between the manifold of the metering gear head and the manifold of the spray head attachment, taken generally along line 2—2 of FIG. 1.

The gear pumps 28a–d are mounted to a manifold 30 carried at the base of the housing 18. As shown in FIG. 2, the output of gear pump 28d, for example, is connected to the inlet of eight individual, adhesive supply passageways 32 formed in the manifold 30. The gear pump 28d is operable to pump precise quantities of hot melt adhesive into each of the adhesive supply passageways 32 for discharge through their outlets 34 formed on an outer surface face 36 of manifold 30. The gear pumps 28a–c each feed a group of eight adhesive supply passageways (not shown) so that a total of 32 individual adhesive supply passageways 32 are formed in manifold 30, each having an outlet 34 on its outer surface 36.

Figure 3:
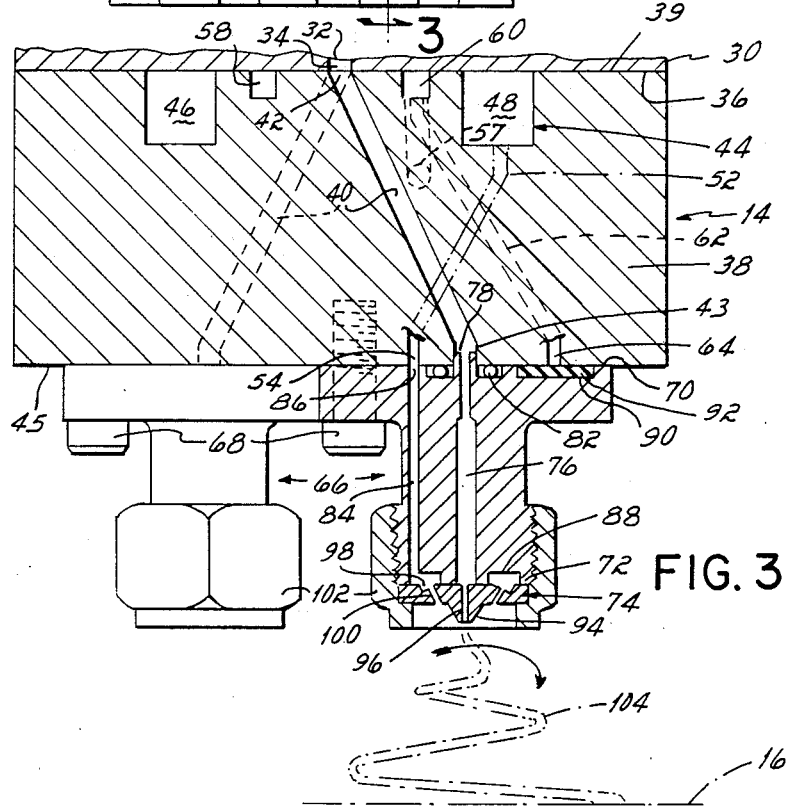
FIG. 3 is a cross sectional view of the manifolds and a nozzle herein taken generally along line 3—3 of FIG. 2.

Referring now to FIGS. 1–3, the spray head attachment 14 of this invention is illustrated in detail. The spray head attachment 14 comprises a distribution manifold 38 having an inner surface 39 which is mounted by bolts (not shown) to the outer surface 36 of manifold 30. The distribution manifold 38 is formed with a total of 32 adhesive connector passageways 40, one for each of the adhesive supply passageways 32 in the manifold 30. As shown in FIG. 2, for example, eight of the adhesive connector passageways 40 are formed in distribution manifold 38 near the outlet of gear pump 28d. Each of these adhesive connector passageways 40 has an inlet 42 at the inner surface 39 of distribution manifold 38 which mates with an outlet 34 of an adhesive supply passageway 32 in the manifold 30, and an outlet 43 which terminates at a discharge surface 45 of distribution manifold 38. The other gear pumps 28a–c feed an identical group of eight adhesive supply passageways 40, some of which are shown in FIG. 4. A gasket (not shown) can be interposed between the mating faces of the manifolds 30, 38 to create a fluid tight seal therebetween.

As best shown in FIGS. 3 and 4, the distribution manifold 38 is formed with a continuous air channel 44 having opposed sides 46, 48 extending longitudinally along the distribution manifold 38. This air channel 44 receives pressurized air from a source (not shown) connected to a pair of inlets 50, 51 on opposite sides of the distribution manifold 38. A total of 32 air connector passageways 52, only some of which are shown in FIGS. 3 and 4, extend from an inlet formed in one of the sides 46, 48 of air channel 44 to the discharge surface 45 of distribution manifold 38 where each terminates in an outlet 54.

The distribution manifold 38 is also formed with a continuous recirculation channel 56 having opposed sides 58, 60 extending parallel to one another and inwardly relative to the sides 46, 48 of the air channel 44. In the embodiment illustrated in FIGS. 1–3, the recirculation channel 56 is connected at one end to an outlet passageway 57, which, in turn, is connected by a return line 59 to the adhesive source 61 which supplies hot melt adhesive to the metering gear head 12. Alternatively, the recirculation channel 56 is connected to the metering gear head manifold 30 by a return line (not shown). A total of 32 recirculation passageways 62, some of which are shown in FIG. 3, are formed in distribution manifold 38 and each extends between an outlet formed in one of the sides 58, 60 of the recirculation channel 56 and an inlet 64 at the discharge surface 45 of manifold 38.

As best shown in FIGS. 3 and 4, the adhesive connector passageways 40, air connector passageways 52 and recirculation passageways 62 formed in distribution manifold 38 have their outlets 43, 54 and inlet 64, respectively, located in an array of three on the discharge surface 45 of distribution manifold 38. That is, the outlet 43 of one adhesive connector passageway 40, the outlet 54 of one air connector passageway 52 and the inlet 64 of one recirculation passageway 62 are formed in close proximity to one another, in 32 separate arrays, along the longitudinal extent of the distribution manifold 38 at its discharge surface 45. Each array of three outlets 43, 54 and inlet 64 is connected to one nozzle 66 mounted by bolts 68 to the discharge surface 45 of distribution manifold 38. A total of 32 nozzles 66, all of which are shown in FIG. 1, are operable to dispense hot melt adhesive in 32 overlapping spray patterns onto the backing sheet 16 of a hygienic article.

Referring now to FIG. 3, one presently preferred embodiment of a nozzle 66 is shown in detail. The nozzle 66 is formed with an inner face 70 mounted by bolts 68 to the discharge surface 45 of distribution manifold 38, and an outer end 72 which mounts a nozzle attachment 74 discussed in detail below. The nozzle 66 is formed with a central, adhesive discharge passageway 76 extending between the inner face 70 and outer end 72. Preferably, a projection 78 extends outwardly from the inner face 70 of nozzle 66 at the inner end of adhesive discharge passageway 76 which is formed to mate with the outlet 43 of an adhesive connector passageway 40 in distribution manifold 38. An annular recess is formed in the nozzle 66 around the projection 78 which receives an O-ring 82 forming a seal between the nozzle 66 and distribution manifold 38 thereat.

The nozzle 66 is formed with an air discharge passageway 84 having an inlet 86 at the inner face 70 of nozzle 66 which mates with the outlet 54 of an air connector passageway 52 in the distribution manifold 38. The air discharge passageway 84 terminates at an annular chamber 88 formed in the outer end 72 of nozzle 66 for purposes to become apparent below.

The nozzle 66 is also formed with a recess 90 extending inwardly from its inner face 70 in alignment with the inlet 64 of a recirculation passageway 62 in the distribution manifold 38. In the embodiment of nozzle 66 shown in FIG. 3, the recess 90 receives a seal 92 to prevent leakage of adhesive flowing through recirculation passageway 62, as described below.

The nozzle attachment 74 is disclosed in detail in co-pending U.S. patent application Ser. No. 07/041,712, filed Apr. 23, 1987, now U.S. Pat. No. 4,785,996, and entitled "Adhesive Spray Gun And Nozzle Attachment" to Ziecker et al, the disclosure of which is incorporated by reference in its entirety herein. For purposes of the present discussion, the nozzle attachment 74 is an annular plate having an upper surface which engages the outer end 72 of nozzle 66 and a lower surface formed with a nozzle tip 94. A throughbore 96 is formed between the upper surface of the nozzle attachment 74 and the nozzle tip 94.

An annular, V-shaped groove 98 is formed in the nozzle attachment 74 which extends inwardly from its upper surface toward the lower surface. In the presently preferred embodiment, six air jet bores 100, two of which are shown in FIG. 3, are formed in the nozzle attachment 74 between the annular groove 98 and the lower surface, preferably at an angle of approximately 30° relative to the longitudinal axis of the throughbore 96. The air jet bores 100 are positioned to eject an air jet substantially tangent to the outer periphery of the throughbore 96 for purposes described below.

The nozzle attachment 74 is secured to the outer end 72 of nozzle 66 by a nut 102 having internal threads which mate with threads formed on the outer surface of the nozzle 66. With the nozzle attachment 74 in this position, the throughbore 96 is connected to the adhesive discharge passageway 76 in nozzle 66, and the annular groove 98 is connected to the air chamber 88 formed at the outer end 72 of nozzle 66.

The operation of the dispensing system 10 with the nozzle 66 shown in FIG. 3 is as follows. Heated hot melt adhesive is pumped by the gear pumps 28a–d in the metering gear head 12 through each of the adhesive supply passageways 32 in the metering gear head manifold 30. The adhesive is discharged from the outlets 34 of the passageways 32 in manifold 30 into each of the 32 adhesive connector passageways 40 formed in the distribution manifold 38 of the spray attachment 14. The adhesive is transmitted through the adhesive connector passageways 40 into the adhesive discharge passageway 76 of each of the nozzles 66. At the same time, pressurized air flowing through the air channel 44 in distribution manifold 38 is transmitted through the air connector passageways 52 into the air discharge passageway 84 of each nozzle 66.

The flow of hot melt adhesive through the adhesive discharge passageway 76 in nozzle 66 is transmitted into the throughbore 96 of the nozzle attachment 74 and then discharged through the nozzle tip 94 to form an adhesive bead 104. At the same time the adhesive bead 104 is formed and ejected from the nozzle attachment 74, pressurized air flowing through the air discharge passageway 84 to the chamber 88 formed at the outer end 72 of nozzle 66 is distributed from the chamber 88 into each of the air jet bores 100. The air jet bores 100 are angled relative to the longitudinal axis of the throughbore 96 so that the jets of air flowing therethrough impact the adhesive bead 104 substantially tangent to its outer periphery at a point spaced below the nozzle tip 94. The jets of air attenuate or stretch the adhesive bead 104 forming elongated strands or fibers of hot melt adhesive for deposit onto the backing sheet 16. Additionally, since the air jet bores 100 are oriented to direct jets of air tangent to the outer periphery of the adhesive bead 104, the adhesive bead 104 and adhesive fibers formed therefrom are rotated or twisted in a compact spiral path toward the backing sheet 16. This produces a controlled spiral pattern of adhesive on the backing sheet 16 having the desired width and thickness.

Referring now to FIGS. 5–8, a number of structures are illustrated for attachment to the distribution manifold 38 which provide flexibility in the type of spray pattern and/or location of the spray pattern of adhesive applied to the backing sheet 16. For example, in some instances it may be desirable or necessary to discharge less than 32 individual patterns of adhesive onto the backing sheet 16 in which case some of the adhesive connector passageways 40 in distribution manifold 38 must be blocked. Alternatively, it may be desirable to apply a thin adhesive bead at some locations along the backing sheet 16, and a spiral spray pattern of adhesive in fiber or strand form at other locations thereon. In still another application, it may be desirable or necessary to spray only air from some of the nozzles located along the length of the distribution manifold 38, particularly at the outermost edges thereof. The structures illustrated in FIGS. 5–8 provide for each of these alternative methods of operating the dispensing system 10 of this invention.

Referring now to FIG. 5, a blocking plate 116 is mounted by bolts 117 to the discharge surface 45 of distribution manifold 38 over the outlets 43, 54 and the inlet 64 of one group of adhesive connector passageways 40, air connector passageways 52 and recirculation passageways 62, respectively, formed in distribution manifold 38. The blocking plate 116 is formed with an internal passageway 120 extending between a recess 122 aligned with the outlet 43 of an adhesive connector passageway 40 in manifold 38, and a second recess 124 aligned with the inlet 64 of a recirculation passageway 62 in manifold 38.

Adhesive flowing through the adhesive connector passageway 40 in distribution manifold 38 thus enters the recess 122 of blocking plate 116, flows through the internal passageway 120 and then through the second recess 124 into the recirculation passageway 62 of distribution manifold 38. The flow of air through air connector passageway 52 in manifold 38 is blocked by the inner surface 119 of blocking plate 116. The blocking plate 116 is therefore effective to eliminate the flow of both air and adhesive from one location along the distribution manifold 38 and return the adhesive to the adhesive source 61 via recirculation passageway 62, recirculation channel 56 and return line 59 so that no adhesive is applied to backing sheet 16 at this location on distribution manifold 38.

Referring now to FIGS. 6 and 7, two alternative embodiments of nozzle 66 and/or nozzle attachment 74 are illustrated, both of which are adapted to apply a thin adhesive bead 129 or 133 onto the backing sheet 16. The nozzle 128 of FIG. 6 is identical to nozzle 66 except for the elimination of an air discharge passageway in nozzle 128. Pressurized air flowing through the air connector passageway 52 in distribution manifold 38 is blocked by the inner face 130 of nozzle 128 so that no air is supplied to the air jet bores 100 of nozzle attachment 74. Adhesive supplied to the adhesive discharge passageway 76 of nozzle 128 from the adhesive connector passageway 40 in manifold 38 is thus discharged from the throughbore 96 in nozzle attachment 74 as a thin adhesive bead 129 for deposit onto the backing sheet 16. All other structure of nozzle 128 is identical to that of nozzle 66 and is given the same reference numerals in FIG. 6.

Referring to FIG. 7, the nozzle 66 is illustrated with an alternative embodiment of a nozzle attachment 132. The nozzle attachment 132 is identical to that of nozzle attachment 74 except that the air jet bores in nozzle attachment 132 are eliminated. The flow of adhesive is permitted through the throughbore 134 of nozzle attachment 132 to form a thin adhesive bead 133 on a backing sheet 16, but the flow of air through the air discharge passageway 84 and chamber 88 of nozzle 66 is blocked by the upper surface 136 of nozzle attachment 132.

Referring now to FIG. 8, it is contemplated that in some applications it may be necessary to discharge a stream of air without adhesive, particularly at the outer edges of distribution manifold 38. This may be required to obtain acceptable spray patterns on the backing sheet 16 near the outer edges of distribution manifold 38. In the embodiment illustrated in FIG. 8, a nozzle 138 is provided which is identical to nozzle 66 except for the elimination of an adhesive discharge passageway in nozzle 138. The nozzle 138 is formed with a recess 140 at its inner face 142 in alignment with the outlet 43 of adhesive connector passageway 40 which mounts an O-ring seal 144. An internal channel 146 extends from the recess 140 to a second recess 148 which aligns with the inlet 64 of recirculation passageway 62 in the distribution manifold 38. This second recess 148 mounts an O-ring seal 150. The remaining structure in nozzle 138 which is common to that of nozzle 66 is given the same reference numbers in FIG. 8.

Adhesive discharged from the adhesive connector passageway 40 in distribution manifold 38 thus flows into the recess 140 of nozzle 138, through the internal passageway 146 and out the second recess 148 to the recirculation passageway 62 in distribution manifold 38. At the same time, air is directed through the air discharge passageway 84 of nozzle 138 to the nozzle attachment 74 in the same manner as in nozzle 66. The nozzle 138 thus provides for the recirculation of adhesive to the metering gear head 12 and the discharge of air from the nozzle attachment 74.

While the invention has been described with reference to a preferred embodiment, it will understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

For example, the spray head attachment 14 has been illustrated in the Figures as being adapted for use with a metering gear head 12 having four gear pumps 28a–d and a total of 32 adhesive supply passageways 32. It is contemplated that the spray head attachment 14 could be constructed with essentially any number of adhesive, air and recirculation passageways to accommodate other metering gear heads, as desired.

Therefore, it is intended that the invention not be limited to the particular embodiment disclosed as the best mode contemplated for carrying out this invention, but that the invention will include all embodiments falling within the scope of the appended claims.

I claim:

1. Apparatus for spraying hot melt adhesive onto the backing sheet of a hygienic article, comprising:
    a flow metering device having means for discharging a separately metered quantity of hot melt adhesive through each of a plurality of outlets;
    a manifold mounted to said flow metering device, said manifold being formed with adhesive connector passageways each having an inlet communicating with one of said outlets of said flow metering device and an outlet formed on a discharge surface of said manifold, said manifold being formed with air connector passageways each having an inlet adapted to connect to a source of pressurized air and an outlet formed on said discharge surface of said manifold, said outlets of said adhesive connector passageways and said outlets of said air connector passageways being arranged in arrays on said discharge surface of said manifold each consisting of an outlet of one adhesive connector passageway and an outlet of one air connector passageway;
    a nozzle mounted to said discharge surface of said manifold over one of said arrays of an adhesive connector passageway outlet and an air connector passageway outlet, said nozzle being formed with an adhesive discharge passageway connected to said outlet of said adhesive connector passageway and an air discharge passageway connected to said outlet of said air connector passageway;
    a nozzle attachment mounted to said nozzle, said nozzle attachment being formed with a through-bore connected to said adhesive discharge passageway of said nozzle for discharging a bead of adhesive, said nozzle attachment being formed with air jet bores connected to said air discharge passageway of said nozzle for directing pressurized air substantially tangent to the outer periphery of said bead of adhesive to form elongated adhesive fibers and to impart a twisting motion to said elongated adhesive fibers for deposition in a spiral spray pattern on the backing sheet of a hygienic article.

2. A spray head attachment adapted for use with a flow metering device for dispensing adhesive onto the backing sheet of a hygienic article, said flow metering device having outlets and means for pumping a separately metered quantity of adhesive through each of said outlets, said spray head attachment comprising:
    a manifold mounted to the flow metering device, said manifold being formed with adhesive connector passageways each having an inlet adapted to connect one of said outlets formed in the flow metering device and an outlet formed on a discharge surface of said manifold, said manifold being formed with air connector passageways each having an inlet adapted to connect to a source of pressurized air and an outlet formed on said discharge surface of said manifold, said outlets of said adhesive connector passageways and said air connector passageways being arranged in arrays on said discharge surface of said manifold consisting of an outlet of one adhesive connector passageway and an outlet of one air connector passageway;
    a nozzle mounted to said discharge surface of said manifold over one of said arrays of an adhesive connector passageway outlet and an air connector passageway outlet, said nozzle being formed with an adhesive discharge passageway connected to said outlet of said adhesive connector passageway and an air discharge passageway connected to said outlet of said air connector passageway;
    a nozzle attachment mounted to said nozzle, said nozzle attachment being formed with a through-bore connected to said adhesive discharge passageway of said nozzle for discharging a bead of adhesive, said nozzle attachment being formed with air jet bores connected to said air discharge passageway of said nozzle for directing pressurized air substantially tangent to the outer periphery of said bead of adhesive to form elongated adhesive fibers and to impart a twisting motion to said elongated adhesive fibers for deposition in a spiral spray pattern on the backing sheet of a hygienic article.

3. The spray head attachment of claim 2 in which said manifold is formed with a substantially rectangular-shaped air channel communicating with a source of pressurized air, said air channel being formed with opposed sides extending parallel to the longitudinal axis of said manifold, each of said air connector passageways having an inlet at one of said opposed sides of said air channel and an outlet at said discharge surface of said manifold.

4. A spray head attachment adapted for use with a flow metering device for dispensing adhesive onto the backing sheet of a hygienic article, said flow metering device having outlets and means for pumping a separately metered quantity of adhesive through each of said outlets, said spray head attachment comprising:
    a manifold mounted to the flow metering device, said manifold being formed with adhesive connector passageways each having an inlet adapted to connect to one of said outlets formed in the flow metering device, air connector passageways adapted to connect to a source of pressurized air and recirculation passageways, each of said adhesive connector passageways and said air connector passageways having an outlet formed on a discharge surface of said manifold and each of said recirculation passageways having an inlet formed on said discharge surface of said manifold, said outlets and inlets being arranged in arrays each consisting of an outlet of one adhesive connector passageway, an outlet of one air connector passageway and an inlet of one recirculation passageway;

a nozzle mounted to said discharge surface of said manifold over one of said arrays of an adhesive connector passageway outlet, an air connector passageway outlet and a recirculation passageway inlet, said nozzle being formed with an adhesive discharge passageway connected to said outlet of said adhesive connector passageway and an air discharge passageway connected to said outlet of said air connector passageway;

a nozzle attachment mounted to said nozzle, said nozzle attachment being formed with a throughbore connected to said adhesive discharge passageway of said nozzle for discharging a bead of adhesive, said nozzle attachment being formed with air jet bores connected to said air discharge passageway of said nozzle for directing pressurized air substantially tangent to the outer periphery of said bead of adhesive to form elongated adhesive fibers and to impart a twisting motion to said elongated adhesive fibers for deposition in a spiral spray pattern on the backing sheet of a hygienic article.

5. The spray head attachment of claim 4 in which said manifold is formed with a substantially rectangular-shaped air channel communicating with a source of pressurized air, said air channel being formed with opposed sides extending parallel to the longitudinal axis of said manifold, each of said air connector passageways having an inlet of one of said opposed sides of said air channel and an outlet at said discharge surface of said manifold.

6. The spray head attachment of claim 4 in which said manifold is formed with a recirculation channel adapted to communicate with said flow metering device, said recirculation channel being formed in a substantially rectangular shape having opposed sides extending parallel to the longitudinal axis of said manifold, each of said recirculation passageways having an inlet at one of said opposed sides of said recirculation channel and an outlet at said discharge surface of said manifold.

7. The spray head attachment of claim 6 in which said nozzle is formed with a recess in alignment with said outlet of one of said recirculation passageways in said manifold, said recess mounting a seal for sealing said recirculation passageway.

8. The spray head attachment of claim 6 further including a blocking plate having an inner surface mounted to said discharge surface of said manifold over one of said arrays of an adhesive connector passageway outlet, an air connector passageway outlet and a recirculation passageway inlet, said blocking plate being formed with an internal passageway having an inlet connected to said outlet of said adhesive connector passageway and an outlet connected to said inlet of said recirculation passageway for transmitting adhesive therebetween, said blocking plate blocking the flow of pressurized air from said air connector passageway in said manifold into said nozzle and recirculating the flow of adhesive from said outlet of said adhesive connector passageway in said manifold to said recirculation channel in said manifold.

9. A spray head attachment adapted for use with a flow metering device for dispensing adhesive onto the backing sheet of a hygienic article, said flow metering device having outlets and means for pumping a separately metered quantity of adhesive through each of said outlets, said spray head attachment comprising:

a manifold mounting to the flow metering device, said manifold being formed with adhesive connector passageways each having an inlet adapted to connect to one of said outlets formed in the flow metering device, air connector passageways adapted to connect to a source of pressurized air and recirculation passageways, each of said adhesive connector passageways and said air connector passageways having an outlet formed on a discharge surface of said manifold and each of said recirculation passageways having an inlet formed on said discharge surface of said manifold, said outlets and inlets being arranged in arrays each consisting of an outlet of one adhesive connector passageway, an outlet of one air connector passageway and an inlet of one recirculation passageway;

a nozzle having an outer end and an inner surface mounted to said discharge surface of said manifold over one of said arrays of an adhesive connector passageway outlet, an air connector passageway outlet and a recirculation passageway inlet, said nozzle being formed with an adhesive discharge passageway extending between said inner surface and said outer end thereof, said adhesive discharge passageway having an inlet connected to said outlet of said adhesive connector passageway of said manifold, said inner surface of said nozzle sealing said outlet of said air connector passageway and said inlet of said recirculation passageway at said discharge surface of said manifold;

a nozzle attachment mounted to said outer end of said nozzle, said nozzle attachment being formed with a throughbore connected to said adhesive discharge passageway of said nozzle for discharging a bead of adhesive onto the backing sheet of a hygienic article.

10. A spray head attachment adapted for use with a flow metering device for spraying hot melt adhesive onto the backing sheet of a hygienic article, said flow metering device having outlets and means for pumping a separately metered quantity of adhesive through each of said outlets, said spray head attachment comprising:

a manifold mounted to the flow metering device, said manifold being formed with adhesive connector passageways each having an inlet adapted to connect to one of said outlets formed in the flow metering device, air connector passageways adapted to connect to a source of pressurized air and recirculation passageways, each of said adhesive connector passageways and said air connector passageways having an outlet formed on a discharge surface of said manifold and each of said recirculation passageways having an inlet formed on said discharge surface of said manifold, said outlets and inlets being arranged in arrays each consisting of an outlet of one adhesive connector passageway, an outlet of one air connector passageway and an inlet of one recirculation passageway;

a nozzle mounted to said discharge surface of said manifold over one of said arrays of an adhesive connector passageway outlet, an air connector passageway outlet and a recirculation passageway inlet, said nozzle being formed with an adhesive discharge passageway connected to said outlet of said adhesive connector passageway and an air discharge passageway connected to said outlet of said air connector passageway;

a nozzle attachment having a nozzle tip and an inner surface mounted to said outer end of said nozzle, said nozzle attachment being formed with a throughbore having an inlet connected to said adhesive discharge passageway in said nozzle and a discharge orifice at said nozzle tip for discharging a head of adhesive onto the backing sheet of a hygienic article, said inner surface of said nozzle attachment blocking the flow of air through said air discharge passageway at said outlet end of said nozzle.

11. A spray head attachment for use with a flow metering device for spraying hot melt adhesive onto the backing sheet of a hygienic article, said flow metering device having outlets and means for pumping a separately metered quantity of adhesive through each of said outlets, said spray head attachment comprising:

a manifold mounted to the flow metering device, said manifold being formed with adhesive connector passageways each having an inlet adapted to connect to one of said outlets formed in the flow metering device, air connector passageways adapted to connect to a source of pressurized air and recirculation passageways, each of said adhesive connector passageways and said air connector passageways having an outlet formed on a discharge surface of said manifold and each of said recirculation passageways having an inlet formed on said discharge surface of said manifold, said outlets and inlets being arranged in arrays each consisting of an outlet of one adhesive connector passageway, an outlet of one air connector passageway and an inlet of one recirculation passageway;

at least one first nozzle mounted to said discharge surface of said manifold over one of said arrays of an adhesive connector passageway outlet, an air connector passageway outlet, and a recirculation passageway inlet, said first nozzle being formed with an adhesive discharge passageway connected to said outlet of said adhesive connector passageway and an air discharge passageway connected to said outlet of said air connector passageway;

a nozzle attachment mounted to said nozzle, said nozzle attachment being formed with a throughbore connected to said adhesive discharge passageway of said first nozzle for discharging a bead of adhesive, said nozzle attachment being formed with air jet bores connected to said air discharge passageway of said first nozzle for directing pressurized air substantially tangent to the outer periphery of said bead of adhesive to form elongated adhesive fibers and to impart a twisting motion to said elongated adhesive fibers for deposition in a spiral spray pattern on the backing sheet of a hygienic article;

at least one second nozzle mounted to said discharge surface of said manifold over another of said arrays of an adhesive connector passageway outlet, an air connector passageway outlet and a recirculation passageway inlet, said second nozzle being formed with an internal passageway having an inlet connected to said outlet of said adhesive connector passageway of said manifold and an outlet connected to said inlet of said recirculation passageway of said manifold for transmitting adhesive therebetween, said second nozzle being formed with an air discharge passageway connected to said outlet of said air connector passageway of said manifold;

said nozzle attachment being mounted to said second nozzle so that said air jet bores of said nozzle attachment connect to said air discharge passageway of said nozzle for discharging air toward the backing sheet of a hygienic article.

* * * * *